United States Patent [19]

Hongo et al.

[11] Patent Number: 4,991,589
[45] Date of Patent: Feb. 12, 1991

[54] ULTRASONIC IMAGING APPARATUS

[75] Inventors: Hironobu Hongo, Ootawara; Eiichi Shiki, Tochigi, both of Japan

[73] Assignee: Kabushiki Kaisha Toshiba, Kawasaki, Japan

[21] Appl. No.: 434,483

[22] Filed: Nov. 9, 1989

Related U.S. Application Data

[63] Continuation of Ser. No. 246,105, Sep. 19, 1988, abandoned.

[30] Foreign Application Priority Data

Sep. 22, 1987 [JP] Japan .................................. 62-237790

[51] Int. Cl.⁵ .............................................. A61B 8/00
[52] U.S. Cl. .......................................... 128/661.09
[58] Field of Search ................................... 128/661.09

[56] References Cited

U.S. PATENT DOCUMENTS

| | | | |
|---|---|---|---|
| 3,954,098 | 5/1976 | Dick et al. ................ | 128/2.05 Z |
| 4,271,842 | 6/1981 | Specht et al. ................ | 128/661 |
| 4,318,413 | 3/1982 | Iinuma et al. ............... | 128/660.05 |
| 4,436,763 | 8/1984 | Koyano et al. .............. | 128/660.04 |
| 4,501,279 | 2/1985 | Seo ............................. | 128/661.1 |
| 4,509,525 | 4/1985 | Seo ............................. | 128/660.05 |
| 4,572,202 | 2/1986 | Thomenius .................. | 128/660 |

FOREIGN PATENT DOCUMENTS 3614688A 10/1986 Fed. Rep. of Germany .

*Primary Examiner*—Francis Jaworski
*Attorney, Agent, or Firm*—Finnegan, Henderson, Farabow, Garrett, and Dunner

[57] ABSTRACT

In response to heartbeat signals produced by an ECG adapted to detect heartbeats of a subject, an ROI (region of interest) of the subject is scanned plural times to produce a plurality of frames of Doppler image information. In this case, the starts of the scans of the ROI are sequentially delayed from corresponding heartbeat signals in increments of a regular time interval. Each frame of image information is stored in a frame memory in the form of divided sub-frame signals. Corresponding sub-frame signals of the frame signals are read from the frame memory and then synthesized to reconstruct one frame image.

6 Claims, 5 Drawing Sheets

ULTRASONIC IMAGING APPARATUS

This application is a continuation of application Ser. No. 07/246,105, filed Sept. 19, 1988, and now abandoned.

BACKGROUND OF THE INVENTION

1. Field of the Invention

The present invention relates to an ultrasonic imaging apparatus for displaying a B-mode image or two-dimensional image of blood-flow velocity, using ultrasonic waves and, more particularly, to an ultrasonic imaging apparatus which, with the aid of its visual image, is well suited for examining the heart of a patient.

2. Description of the Related Art

An ultrasonic diagnosis apparatus for forming a B-mode image by means of the ultrasonic imaging technique makes use of an array ultrasonic transducer in which many ultrasonic transducer elements are arranged in a line. When linear scanning is performed by means of the array ultrasonic transducer, a fixed number of ultrasonic transducer elements are driven as a group. To focus an ultrasonic beam, in this case, the ultrasonic transducer elements forming the group are driven at different times; more precisely the transducers located at either end of the group are driven first, with the center transducer being the last to be driven. By driving the array transducer for each of transducer-element groups which are shifted in position one element by one element in the array direction, i.e., the scanning direction, ultrasonic beams corresponding to the respective transducer-element groups or scanning lines can be transmitted in sequence from the array ultrasonic transducer, so that a subject under examination is scanned by the ultrasonic beams.

Echo beams from the subject under examination are received by the same array ultrasonic transducer to be converted into echo signals. The echo signals are subjected to the same delay processing as that to which the transmitted ultrasonic beams were subjected, and are then converted Into a tomograph image signal. The tomography image signal is supplied to a TV monitor device, and a tomograph image is visually displayed.

When, on the other hand, sector scanning is performed, the ultrasonic beams are sequentially transmitted from the ultrasonic transducer in such a way that the subject under examination is scanned in sector fashion, with a given point being designated as the center. In this case, the ultrasonic transducer elements are driven at different times, according to their scanning direction, so that the steering direction of the ultrasonic beam is changed for each scanning line.

In addition to the linear scanning and the sector scanning system as described above, there is a mechanical scanning system in which an ultrasonic transducer is mounted on a mechanical scanning device and is moved thereby to perform ultrasonic scanning.

Ultrasonic echo signals of a subject under examination, obtained by ultrasonic scanning carried out in accordance with the above scanning systems, are processed to produce an image signal which, in general, is visually displayed as a B-mode image (tomograph image).

The blood-flow imaging technique for displaying a blood flow profile has been made feasible owing to the ultrasonic imaging apparatus. The Doppler method is generally used for the blood flow imaging. This is a method for detecting moving substances, such as blood flow, within a living subject utilizing the Doppler effect.

The basic principle of the Doppler method is as follows:

When the blood flow within a living subject is subjected to ultrasonic beams, blood corpuscles are caused to vibrate slightly while moving, and reflect the ultrasonic beams. Thus, the reflected beams are subjected to the Doppler effect. In this case, when the blood corpuscles are moving toward the ultrasonic beams, the frequency of the reflected beams becomes slightly higher than that of the transmitted beams, while when they are moving away therefrom, it becomes slightly lower than that of the transmitted beams. Such a frequency shift can be detected, the amount of change in the frequency being referred to as the Doppler shift frequency. Since the Doppler shift frequency is in proportion to the blood-flow velocity, this enables the blood flow conditions to be then be clearly observed.

According to a conventional blood-flow imaging apparatus working on the above principle to obtain blood-flow information, a predetermined number of ultrasonic pulses are repeatedly transmitted in a given direction, and the resulting echo waves are converted in sequence, into echo signals. The echo signals are then phase detected to obtain phase information signals which are in turn digitized and supplied to a digital filter, which removes therefrom signal components corresponding to entirely or virtually motionless parts within the living subject. The signals passed through the digital filter are frequency-analyzed to detect the Doppler shift frequency corresponding to the blood-flow velocity. The Doppler shift frequency is used as blood-flow information for forming a two-dimensional image or profile of the blood-flow velocity. The blood-flow information may be displayed on a TV monitor, either independently or superposed on B-mode or M-mode information.

To simultaneously display a two-dimensional image of blood-flow velocity, superposed on the B-mode or M-mode image, a Doppler information detecting transducer is provided, separated from or integrated with a linear-or sector-scanning array ultrasonic transducer. For instance, ultrasonic waves are transmitted to a subject in accordance with the sector scan to obtain B-mode information, and ultrasonic pulses are transmitted to the subject to obtain Doppler information. The thus obtained B-mode information and Doppler information are superposed and displayed on the monitor TV.

To obtain high-accuracy blood-flow information, that is, Doppler information, each scan line is scanned plural times, for example, ten times, and a sufficient time corresponding to ten scans is taken to obtain the Doppler information at each sampling point. For this reason, a considerable time of about 100 msec is needed to construct a frame of image. This will result in a significant time difference in a two-dimensional image obtained during this period of time. That is, a significant time difference occurs between the first scan region and the last scan region. Accordingly, even if an image of relatively rapid blood-flow, such as the blood-flow in the heart, is displayed on the entire screen of a display, this would not mean, because of the above time difference, that the blood-flow image were precisely displayed. This will make a correct diagnosis difficult.

SUMMARY OF THE INVENTION

It is accordingly an object of the present invention to provide an ultrasonic imaging apparatus which can reduce the influence of a time difference involved in ultrasonic imaging upon diagnostic images.

According to the present invention, in response to heartbeat signals produced by an ECG adapted to detect heartbeats of a subject under examination, an ROI (region of interest) of the subject is scanned plural times to produce a plurality of frames of Doppler image information. In this case, the scans of the ROI are sequentially delayed from corresponding heartbeat signals in increments of a regular time interval. Each frame of image information is stored in a frame memory in the form of divided sub-frame signals. Corresponding sub-frame signals of the frame signals are selectively read from the frame memory and then synthesized to reconstruct one frame image.

DETAILED DESCRIPTION OF THE PREFERRED EMBODIMENT

Figure 1:
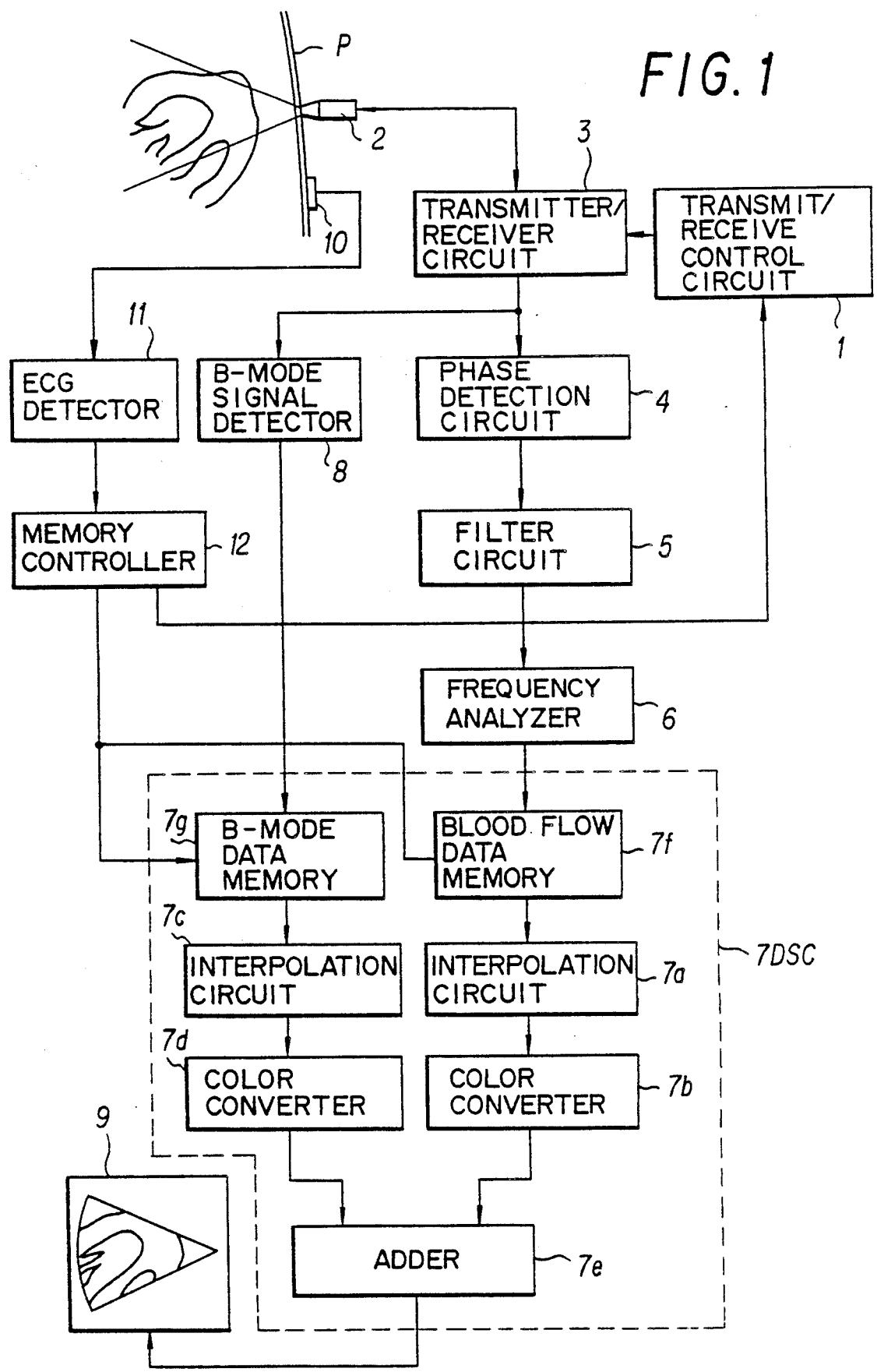
FIG. 1 is a block diagram of an ultrasonic imaging apparatus according to an embodiment of the present invention.

Referring now to FIG. 1, a transmit/receive control circuit 1 is connected to a transmitter/receiver circuit 3 which in turn is coupled to an ultrasonic transducer 2 touched to a portion of a subject P under examination that is near his or her heart. Transmitter/receiver circuit 3 delivers drive pulses to ultrasonic transducer 2 and receives echo signals from ultrasonic transducer 2. An output of transmitter/receiver circuit 3 is coupled to a digital scan converter (DSC) 7 via a phase detector 4, a filter 5 and a frequency analyzer 6. The output of transmitter/receiver circuit 3 is also coupled to DSC 7 via a B-mode detector 8.

Phase detector 4 detects the phase of a Doppler shift signal delivered from transmitter/receiver circuit 3. Filter 5 filters a phase-detected signal from phase detector 3. Frequency analyzer 6 analyzes the frequency of a filtered Doppler signal from filter 5 for conversion to blood-flow information.

In proximity to ultrasonic transducer 2, to subject P is touched an induction electrode 10 which is coupled to an ECG (electrocardiograph) detector 11 which produces ECG signals corresponding to heartbeats of the subject P. ECG detector 11 is coupled to a memory controller 12. Memory controller 12 is constructed as shown in FIG. 2 to provide control signals to transmit/receive control circuit 1 and DSC 7 in response to the ECG signals.

DSC 7 comprises: a blood-flow image data memory 7f, an interpolation circuit 7a and a color conversion circuit 7b which are connected in this sequence; a B-mode image data memory 7g, a B-mode interpolation circuit 7c and a B-mode color conversion circuit 7d which are also connected in this sequence; and an adder circuit 7e for addition of outputs of color conversion L circuits 7b and 7d. An output of adder 7e is connected to a television monitor 9.

Figure 2:
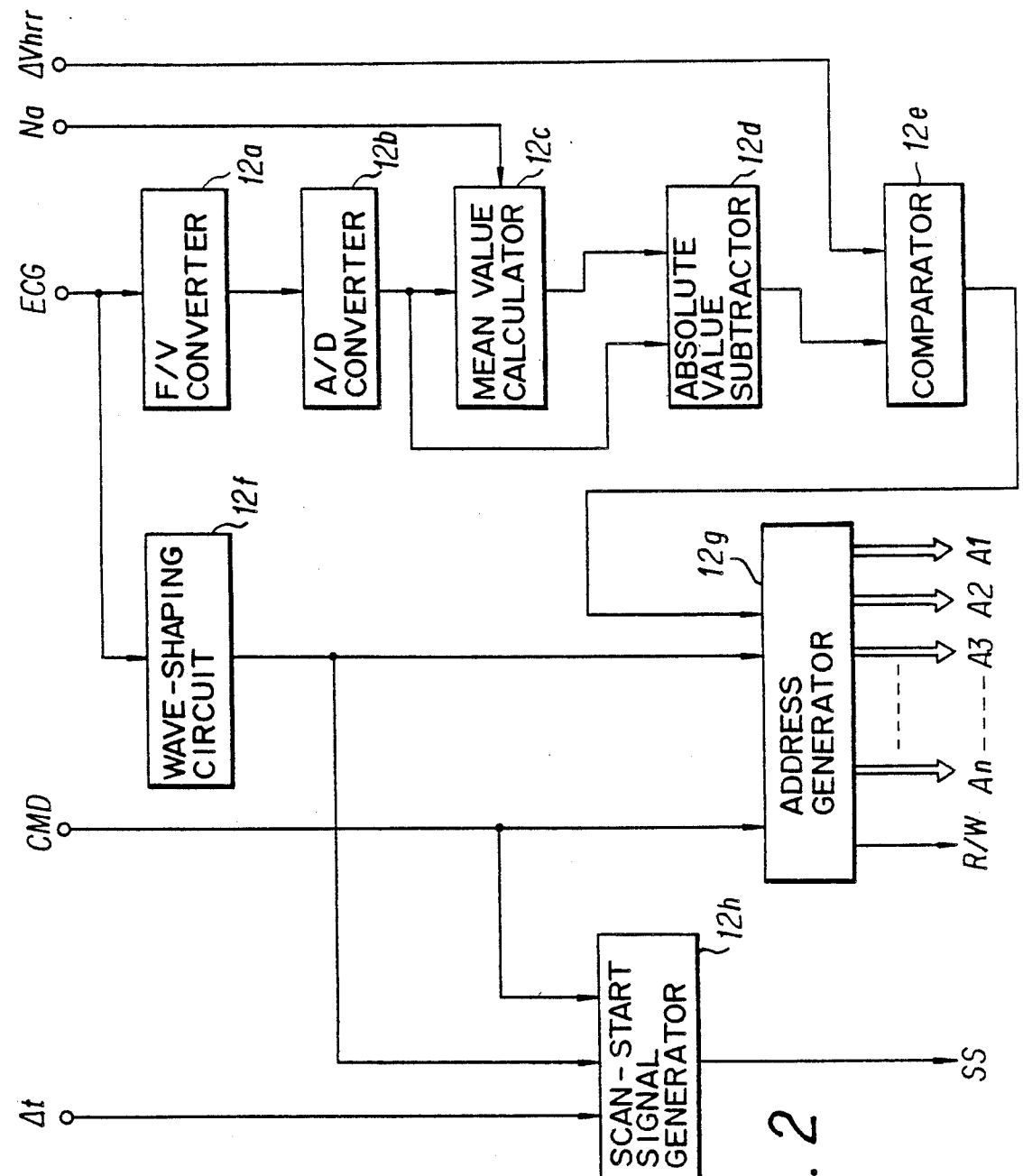
FIG. 2 is a block diagram of the memory controller of FIG. 1.

As shown in FIG. 2, memory controller 12 is comprised of an F/V converter 12a, an A/D converter 12b, an averaging circuit 12c, an absolute-value subtraction L circuit 12d and a comparator which are connected in this sequence, a wave shaper 12f, an address generator 12g and a scan-start signal generator 12h.

F/V converter 12a converts the cycle Hr of the ECG signals from ECG detector 11 to a voltage signal. A/D converter 12b converts the voltage signal to a digital signal. The digital conversion is needed to realize a high-accuracy control. If an analog process can realize the high accuracy control, then the digital process will not be needed. A digital voltage signal Vhr corresponding to the cycle Hr of the ECG signals is applied to averaging circuit 12c. Averaging circuit 12c calculates an average value Vhra of values Vhr obtained in the cycle of the ECG signals over Na cycles thereof in accordance with an average number Na of times of an average-number-of-time signal provided from an external circuit.

Absolute-value subtracter 12d calculates a difference $\Delta Vhr = |Vhr - Vhra|$ between the voltage corresponding to the average value Vhra of the ECG cycle Hr and the voltage Vhr corresponding to its actual value. Comparator 12e makes a comparison between $\Delta Vhr$ and an allowable limit value $\Delta Vhrr$. The comparison is performed to detect ECG signals resulting from arrythmia. That is, by way of example, comparator 12e produces a digital signal Wi which is at a logic 1 (high) level when $\Delta Vhr > \Delta Vhrr$, while at a logic 0 (low) level when $\Delta Vhr \leq \Delta Vhrr$, representing the arrhythmia. The digital signal Wi is entered into address generator 12g as a write disable signal for data memories (7f, 7g). Address generator 12g receives the write disable signal Wi, a timing signal T which is an ECG signal shaped by wave shaper 12f and a mode control signal CMD to produce a write control signal R/W and address information A1-An for memories 7f and 7g in DSC 7.

The mode control signal CMD is 1 when data is acquired, while 0 when data is output, for example. The write control signal R/W varies with the mode control signal CMD. For example, it is 1 when acquired data is written into, while 0 when the data is read from. Scan-start signal generator 12h receives a timing signal corresponding to an ECG signal, the mode control signal CMD and a signal indicative of a staggering interval $\Delta t$ which is separately set and produces a scan-start signal SS from a point of time when data acquisition is started, or when the mode control signal CMD goes from 0 to 1.

Figure 3:
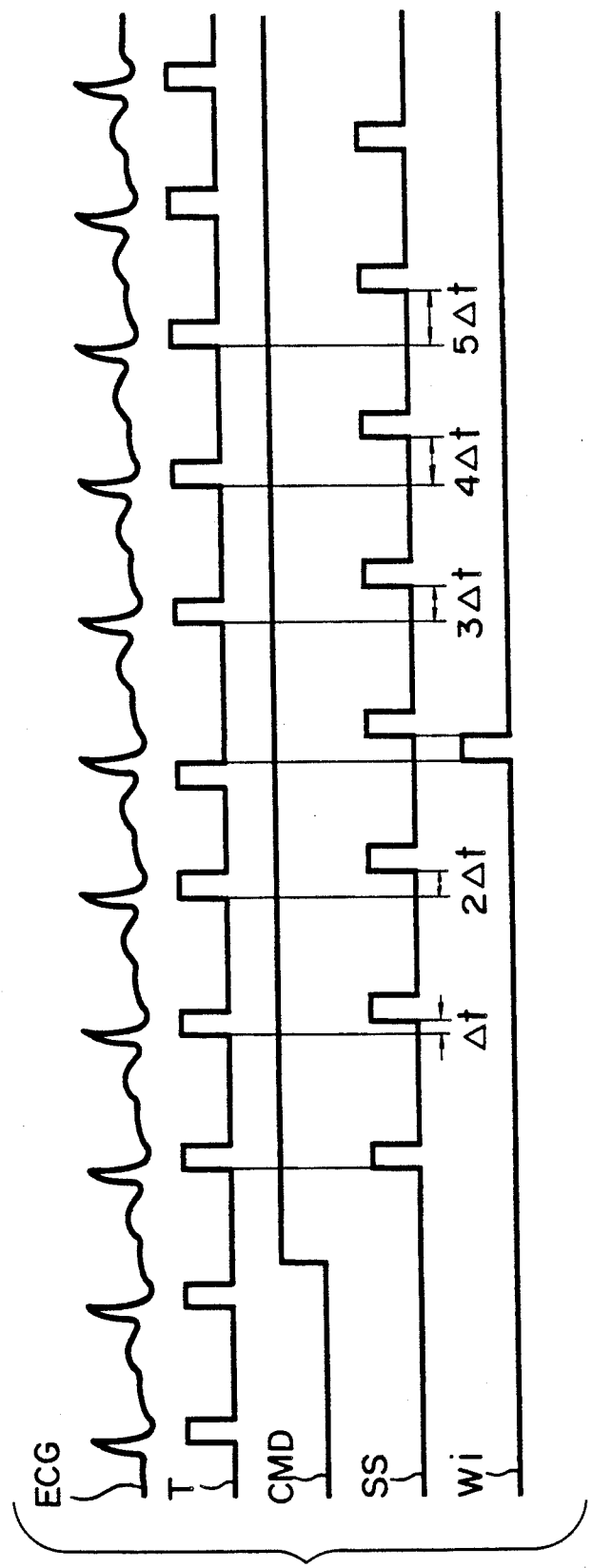
FIG. 3 is a timing diagram of signals used in the memory controller of FIG. 2.

The scan-start signal SS is a signal for instructing the start of acquisition of data in one heartbeat interval and is generated every heartbeat interval after a delay variable by increments of $\Delta t$ as shown in FIG. 3. Scan start signal SS is applied to transmit/receive control circuit 1 which is responsive to the scan-start signal SS to deliver a scan-start timing signal to transmitter/receiver circuit 3. As a result, ultrasonic pulses are emanated from ultrasonic transducer 2 which are sequentially delayed from corresponding ECG pulses, the delays of the ultrasonic pulses being incremented by $\Delta t$ for each of heartbeat intervals. Here $\Delta t$ is a time corresponding to a sub-frame scanning interval.

Figure 4:
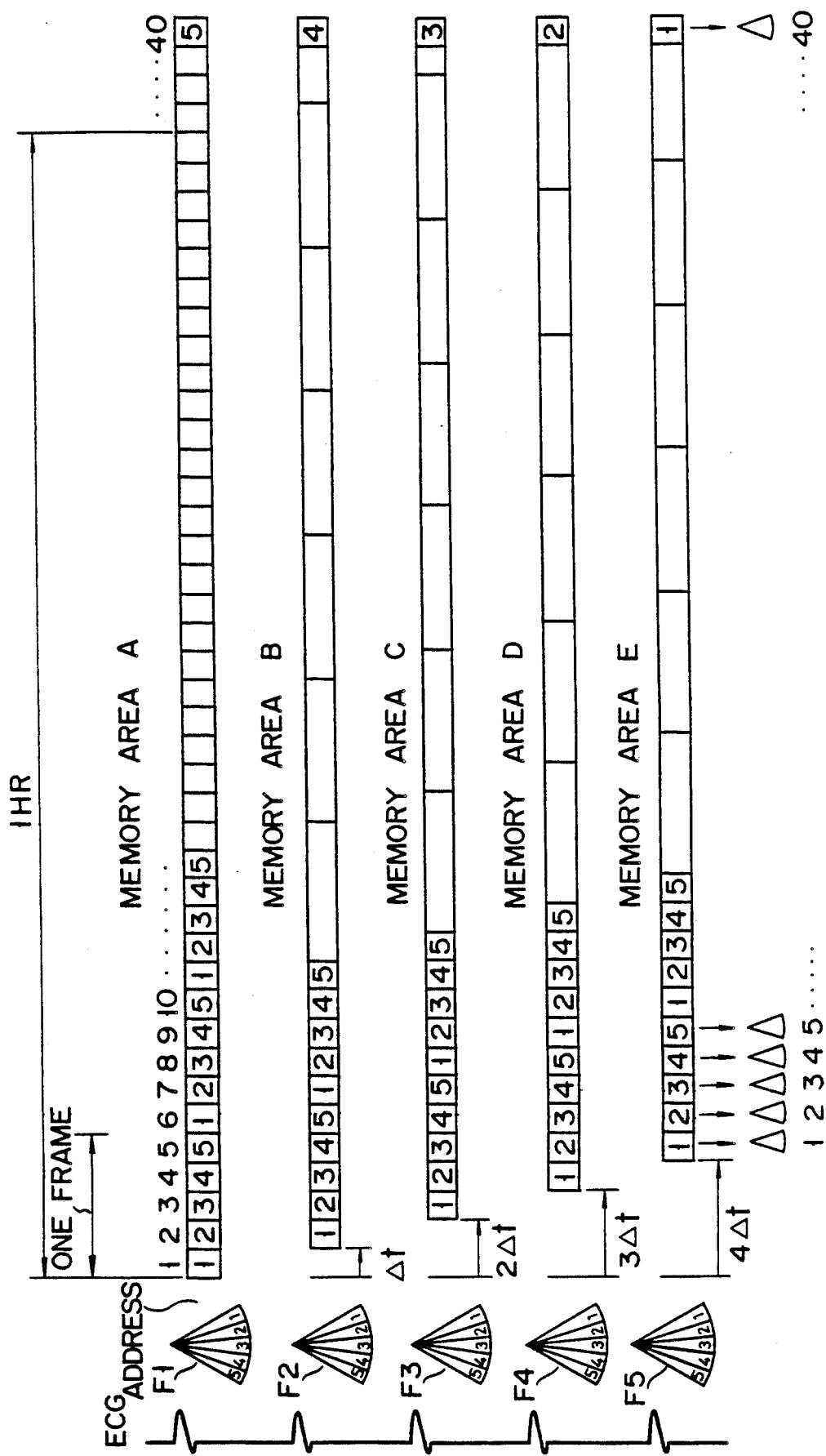
FIG. 4 is a diagram useful for explaining write and read operations for image data.

In operation, ECG detector 11 detects ECG through induction electrode 10 to produce such ECG pulses of a constant cycle as shown in FIG. 3. The ECG signal is shaped into the signal T by wave shaper 12f. The signal T is applied to scan-start signal generator 12h together with the CMD signal and the Δt signal. Circuit 12h responds to the signals T, CMD and Δt to produce and apply the start signal SS to transmit/receive control circuit 1. Transmit/receive control circuit 1 responds to the signal SS to produce and apply a control signal to transmitter/receiver circuit 3. Transmitter/receiver circuit 3 responds to the control signal to output a drive signal to ultrasonic transducer 2. Ultrasonic transducer 2 is driven by the drive signal so as to sector-scan the subject under examination in the B mode or the Doppler mode. That is, in the case of the B mode, one scan is performed for each of scan lines, while, in the Doppler mode, for example, ten scans are performed for each of scan lines. In either scan, the subject is subjected to the sector scan plural times during one heartbeat interval Hr as shown in FIG. 4 with the result that echo signals corresponding to a plurality of frames are taken from ultrasonic transducer 2.

The echo signals taken from ultrasonic transducer 2 by the sector scan are applied to transmitter/receiver circuit 3 for signal processing so that a B-mode signal and a Doppler-mode signal are produced. The Doppler-mode signal is detected by phase detector 4 for application to frequency analyzer 6 via filter 5. Frequency analyzer 6 converts the Doppler signal to blood-flow image data which in turn is applied to blood-flow data memory 7f. On the other hand, B-mode detector 8 detects the B-mode signal and transfers it to B-mode data memory 7g. At this time, address generator 12g of memory controller 12 responds to the signal T from wave shaper 12f to generate address information A1-An. In this case, first, address generator 12g generates address information 1-5 corresponding to sub-frames 1-5 of a first frame. When a memory area A of blood-flow data memory 7f is designated by the address information 1-5, five sub-frames 1-5 of image data are stored in memory area A designated by address information 1-5. Here it is to be understood that each of address information 1, 2, 3, 4, ... specifies an address group for a memory area which can store a sub-frame of image data.

As described above, a plurality of frames of blood-flow image data detected during a first ECG interval are stored in storage area A of memory 7f. When the next ECG signal is output from ECG detector 11, memory controller 12 produces a scan-start signal after a delay of Δt from the ECG signal. In response to this scan-start signal, transmit/receive control circuit 1 applies a control signal to transmitter/receiver circuit 3 which thus applies a drive signal to ultrasonic transducer 2 to sector scan the subject after a delay of Δt from the ECG signal. By this sector scan, a plurality of frames of echo signals in the second interval are taken from ultrasonic transducer 2 and a plurality of sub-frames 1-5 of blood flow data are stored in address locations 2-6 of a storage area B of memory 7f in the same manner as described above.

Subsequently, the subject is subjected to the sector scan after a delay of 2Δt from a third ECG signal, and thus sub-frames 1-5 of blood flow data in the third ECG interval are stored in address locations 3-7 in a storage area C of memory 7f. Furthermore, the subject is sector scanned after delays of 3Δt and 4Δt from fourth and fifth ECG signals with the result that sub-frames 1-5 of blood flow data in the fourth and fifth ECG intervals are formed and stored in address locations 4-8 of a storage area D and address locations 5-9 of a storage area E of memory 7f.

Next, a read operation for the blood flow data stored in memory 7f in the above manner will be described.

For reading operations as well, memory controller 12 produces address information. A memory format of FIG. 4 is depicted in conformity with the axis of abscissa (time axis) according to which a plurality of ECG pulses coincide in time as shown. As can be seen from FIG. 4, by designating address location 5, sub-frames 5-1, which are coincident on the time axis, can be read out from memory areas A-E, respectively, which correspond to the five Hr intervals. Blood flow data of these sub-frames 5-1 are synthesized to produce one frame of blood flow data which is then input to interpolation circuit 7a. Interpolation circuit 7a performs an interpolation process for arranging the blood flow data in a sector form and making up vacant pixels. Blood flow data output from interpolation circuit 7a is input to color conversion circuit 7b for conversion to color image data. The color image data is fed via adder circuit 7e to television monitor 9 on which blood-flow images are visually displayed in colors.

When, as described above, the first frame of image data is reconstructed from the sub-frames of blood flow data and then displayed on the television monitor, the next frame of blood flow data is reconstructed of corresponding sub-frames of blood flow data. In this case, address 6 is designated in each of memory areas A-E. Consequently, the first sub-frame 1 of blood flow data of the second frame stored in memory area A and sub-frames 5-2 of blood flow data of the first frames in memory areas B-E are read out. The read sub-frames 1, 5-2 of blood flow data are synthesized to one frame of image data. In this way, frames of blood flow data are reconstructed in succession and applied to television monitor 9 via interpolation circuit 7a, color conversion circuit 7b and adder circuit 7e. As a result, color blood-flow images which have little time difference among them can be visually displayed.

In the above embodiment, a plurality of memory areas A-E are provided, and address locations 1, 2, 3, 4, ... are used in common with memory areas A-E. However, this is for convenience of description only, not intended to restrict the scope of the present invention.

In the above, description is made of the Doppler mode case. In the case of the B mode, B-mode detector 8 detects B-mode signals from echo signals and stores them in B-mode data memory 7g. As with the Doppler mode, the B mode signals are stored in each of memory areas A-E of memory 7g in the form of frames of data each composed of a plurality of sub-frames of data in response to each of the ECG pulses. These frames of data are interpolated by interpolation circuit 7c and then applied to adder circuit 7e via B-mode color conversion circuit 7d. Adder circuit 7e synthesizes the Doppler image signal and the B-mode image signal and applies a resultant signal to monitor 9.

According to the present invention, as described above, the subject under examination is subjected to a sector scan in response to the R wave of the first ECG signal of ECG signals which are cyclically produced, and then one frame of information is formed and stored in the memory. The subject is subjected to another sector scan from a point of time after a delay of Δt from the R wave of the next ECG signal, and thus a second frame of information is formed and stored in the memory. Further, the subject is sector scanned after a delay of 2Δt from the R wave of the next ECG signal to produce and store a third frame of information in the memory. In this way, a plurality of frames of information having a time difference of Δt between successive frames are formed in succession and stored in the memory.

Plural frames of information thus formed are each divided into sub-frames of information, and corresponding sub-frames of information obtained at the instants delayed by the same amount from R waves are extracted from the plural frames of information (F1–F5) to reconstruct one frame of image. Sub-frames of information for different portions obtained at the same instants after the R waves of ECG signals can be regarded as image information for an event occurred at a point of time in the activity of the heart. Thus, a time difference involved in a reconstructed frame of image will be small. Namely, the sub-frames in a reconstructed frame are in time-phase.

In this case, assuming that the frame scan time is Tf, one frame is divided into sub-frames in number of N = Tf/Δt. The sub-frames are obtained in time-phase at Δt intervals. Address generator 12g outputs the write control signal R/W and address information A1-An so as to write the blood-flow data composed of the sub-frames which are in time-phase into memory 7f adapted for N frames of blood-flow image data and the B mode data into memory 7g adapted for N frames of B mode data. When the deviation ΔVhe of the ECG cycle Hr is larger than a previously set value, the write disable signal Wi becomes 1, with the result that writing into the memory and increasing the staggering interval are inhibited, in which case, in the next heartbeat interval, the data acquisition and writing into the memory are performed under the same condition as the previous heartbeat interval.

In this way, the data acquisition and writing into the memory are continued until the staggering interval Δt reaches the heartbeat cycle Hr, for example, so that N frames of data are obtained by the division and synthesis. After the data acquisition and the writing into the memory have been completed, when the mode control signal CMD is made 0, address generator 12g generates the write control signal R/W and address information A1-An so as to read out the N frames of data sequentially and repeatedly. The read N frames of data are constructed by interpolation circuit 7a, color conversion circuit 7b and adder circuit 7e to N frames of blood-flow image which are then displayed on television monitor 9 repeatedly.

Usually, one-frame scan time in the blood-flow imaging is about 100 msec, and thus the time difference involved in one frame of a blood-flow image is 100 msec at a maximum value. The number of frames is as small as 10 (=1 sec/0.1 sec). According to the present embodiment, the time difference involved in one frame of blood-flow image is decreased to Δt (Δt/Tf times), and the number of frames is increased up to 1 sec/Δtsec (Tf/Δt times). Further, since data obtained when the ECG's disturbance is great is discarded, an image display can be performed which is little affected by the ECG's disturbance.

Figure 5:
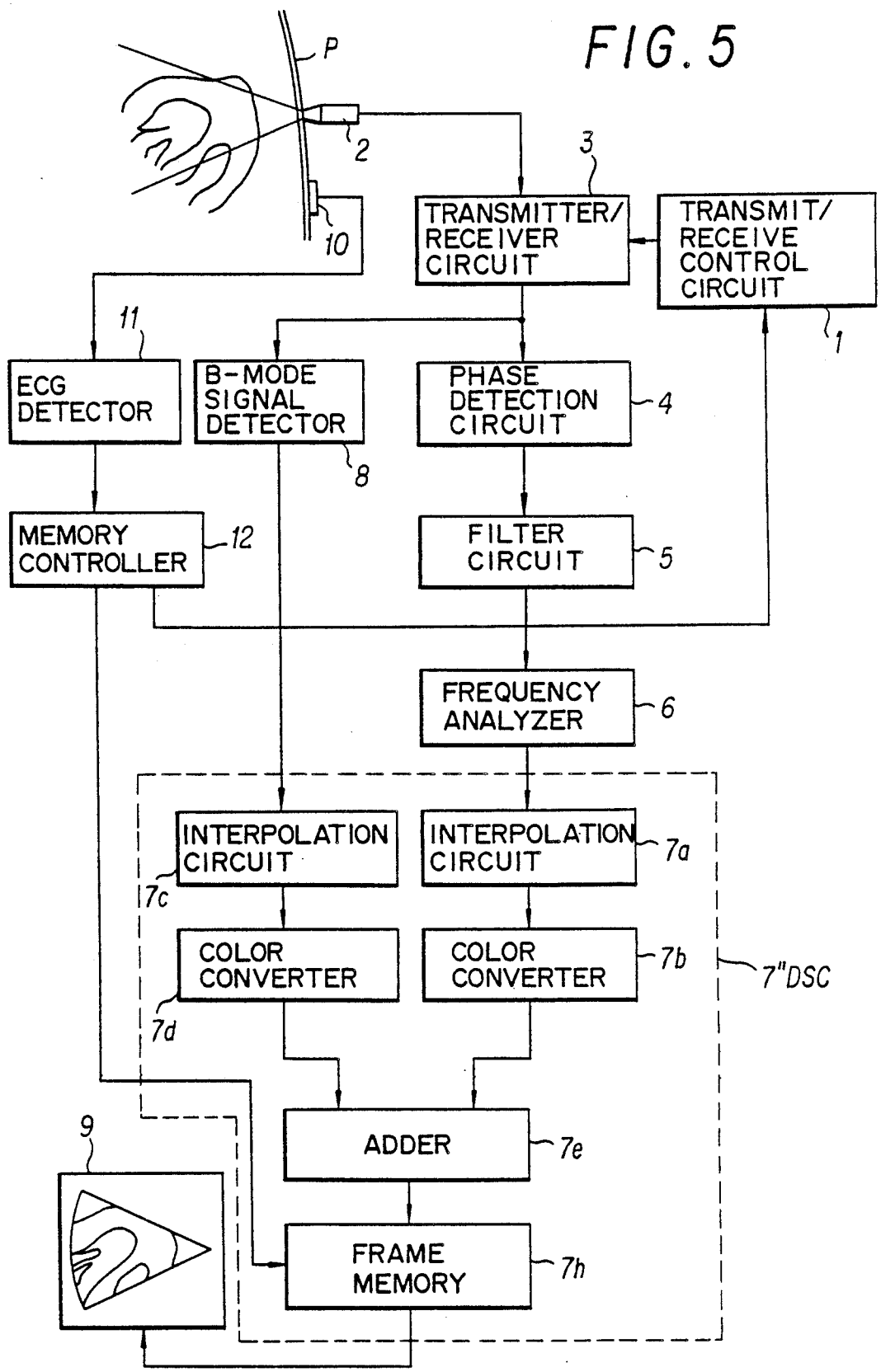
FIG. 5 is a block diagram of an ultrasonic imaging apparatus according to the other embodiment of the present invention.

FIG. 5 shows the other embodiment of the present invention in which DSC 7″ is provided with a frame memory 7h for N frames of blood-flow data in place of memories 7f and 7g. In this embodiment, blood-flow images obtained in succession through interpolation circuit 7a, color conversion circuit 7b, B-mode interpolation circuit 7d and adder circuit 7e are divided and reconstructed by frame memory 7h as shown in FIG. 4. In the above example, the delay time is incremented every heartbeat intervals. Alternatively, the delay time may be decremented. Further, a B-mode image and a two-dimensional blood-flow image are displayed with one superimposed upon the other. Alternatively, the present invention may be applied to apparatus designed to display two-dimensional images only.

What is claimed is:

1. An ultrasonic imaging apparatus comprising:
   ultrasonic transducer means for transmitting ultrasonic beams to scan an region of interest of a subject and receiving echo waves of the ultrasonic beams for conversion to echo signals;
   specific signal generating means for generating a plurality of specific signals periodically;
   transmitter/receiver circuit means coupled to said ultrasonic transducer means and said specific signal generating means for delivering driving signals to said ultrasonic transducer means so that the region of interest is repeatedly scanned in response to the specific signals, the starts of repeated scans in intervals of the specific signals being sequentially staggered in increments or decrements of a regular time interval, receiving echo signals corresponding in number to the scans and processing the echo signals to output a predetermined number of frame signals which are sequentially staggered in increments or decrements of the regular time interval; and
   storing/reconstructing means coupled to said transmitter/receiver circuit means for storing each of the frame signals in the form of divided sub-frame signals, extracting a corresponding sub-frame signal from each of the stored frame signals and synthesizing corresponding sub-frame signals extracted from the frame signals to reconstruct a frame signal.

2. An ultrasonic imaging apparatus according to claim 1, wherein said specific signal generating means comprises ECG signal means for detecting periodic ECG signals; and means responsive to the ECG signals for sequentially producing scan-start signals which are sequentially staggered in increments or decrements of a predetermined time interval corresponding to a sub-frame scan interval; and wherein said transmitter/receiver circuit means includes means responsive to the scan-start signals for sequentially delivering the drive signals.

3. An ultrasonic imaging apparatus according to claim 1, wherein said storing/reconstructing means includes storage means for storing the sub-frame signals of the frame signals; and addressing means for outputting address information to said storage means to write and read the sub-frame signals into and from said storage means, said addressing means outputting write address information in response to the specific signals produced by said specific signal generating means.

4. An ultrasonic imaging apparatus according to claim 3, wherein said specific signal generating means comprises means for detecting ECG signals; and wherein said addressing means comprises arrythmia detecting means for detecting arrythmia from the ECG signals to produce an arrythmia detect signal; and means responsive to the arrythmia detect signal for inhibiting the frame signals from being written into.

5. An ultrasonic imaging apparatus according to claim 4, wherein said arrythmia detecting means comprises means for calculating an average value of the ECG signals; difference detecting means for detecting a difference between the average value and an actual value of the ECG signals; and means for comparing the difference with an allowable value to apply to said addressing means a write inhibiting signal when the difference is above the allowable value.

6. An ultrasonic imaging apparatus comprising:
ultrasonic transducer means for transmitting ultrasonic beams to scan an region of interest of a subject in a B mode and a Doppler mode and receiving echo waves of the ultrasonic beams for conversion to echo signals corresponding to the B mode and the Doppler mode;
specific signal generating means for generating a plurality of specific signals periodically;
transmitter/receiver circuit means coupled to said ultrasonic transducer means and said specific signal generating means for delivering driving signals to said ultrasonic transducer means so that the region of interest is repeatedly scanned in response to the specific signals, the starts of repeated scans in intervals of the specific signals being sequentially staggered in increments or decrements of a regular time interval, receiving echo signals corresponding in number to the scans and processing the echo signals to output a predetermined number of B-mode frame signals which are sequentially staggered in increments or decrements of the regular time interval and a predetermined number of Doppler-mode frame signals which are sequentially staggered in increments or decrements of the regular time interval;
synthesizing means coupled to said transmitter/receiver circuit means for synthesizing the B-mode frame signals and the Doppler-mode signals to produce synthesized frame signals; and
storing/reconstructing means coupled to said synthesizing means for storing each of the synthesized frame signals in the form of divided sub-frame signals, extracting a corresponding sub-frame signal from each of the stored frame signals and synthesizing corresponding sub-frame signals extracted from the frame signals to reconstruct a frame signal.

* * * * *

UNITED STATES PATENT AND TRADEMARK OFFICE
CERTIFICATE OF CORRECTION

PATENT NO. : 4,991,589

DATED : February 12, 1991

INVENTOR(S) : Hironobu Hongo et al.

It is certified that error appears in the above-identified patent and that said Letters Patent is hereby corrected as shown below:

Claim 6, column 9, line 14, change "an" to --a--.

Signed and Sealed this

Twentieth Day of April, 1993

Attest:

MICHAEL K. KIRK

Attesting Officer

Acting Commissioner of Patents and Trademarks